Figure 3:
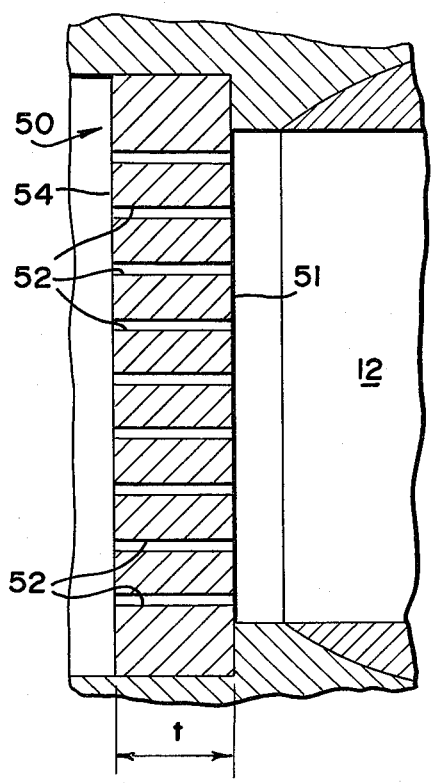

United States Patent [19]
Fletcher et al.

[11] 3,938,367
[45] Feb. 17, 1976

[54] SAMPLER OF GAS BORNE PARTICLES

[76] Inventors: James C. Fletcher, Administrator of the National Aeronautics and Space Administration, with respect to an invention of Charles G. Miller, Pasadena; James B. Stephens, La Crescenta, both of Calif.

[22] Filed: Mar. 28, 1975

[21] Appl. No.: 563,283

[52] U.S. Cl.................. 73/28; 55/261; 73/421.5 R
[51] Int. Cl.².......................................... G01N 15/00
[58] Field of Search.......... 73/28, 421.5 R, 421.5 A; 55/83, 261

[56] References Cited
UNITED STATES PATENTS

| | | | |
|---|---|---|---|
| 3,478,600 | 11/1969 | Lynn | 73/28 |
| 3,819,330 | 6/1974 | Creighton | 73/421.5 A |

*Primary Examiner*—S. Clement Swisher
*Attorney, Agent, or Firm*—Monte F. Mott; Wilfred Grifka; John R. Manning

[57] ABSTRACT

An atmosphere sampler includes a very thin filter element with straight-through holes on the order of $1\mu$. A sample of air with particles to be examined is driven by means of a pressurized low molecular weight gas, e.g., He to the filter element front side. A partial vacuum may be present at the back side of the filter element. The pressure differential across the filter element is just below the rupture point of the filter element. By admixing a low molecular weight gas as the carrier gas with the air sampler the velocity with which the air sample is driven to the filter element is maximized for the particular pressure differential across the filter element, so that at least some particles with diameters less than the hole diameter do not follow changes in the air stream line direction as it passes through the filter element holes and therefore the smaller diameter particles are deposited on the filter element. When using a filter element of plastic material of a thickness on the order of $10\mu$, a stainless steel back-up plate and a diffusion member are used to support the filter element when subjected to a pressure differential on the order of a few hundred atmospheres.

10 Claims, 6 Drawing Figures

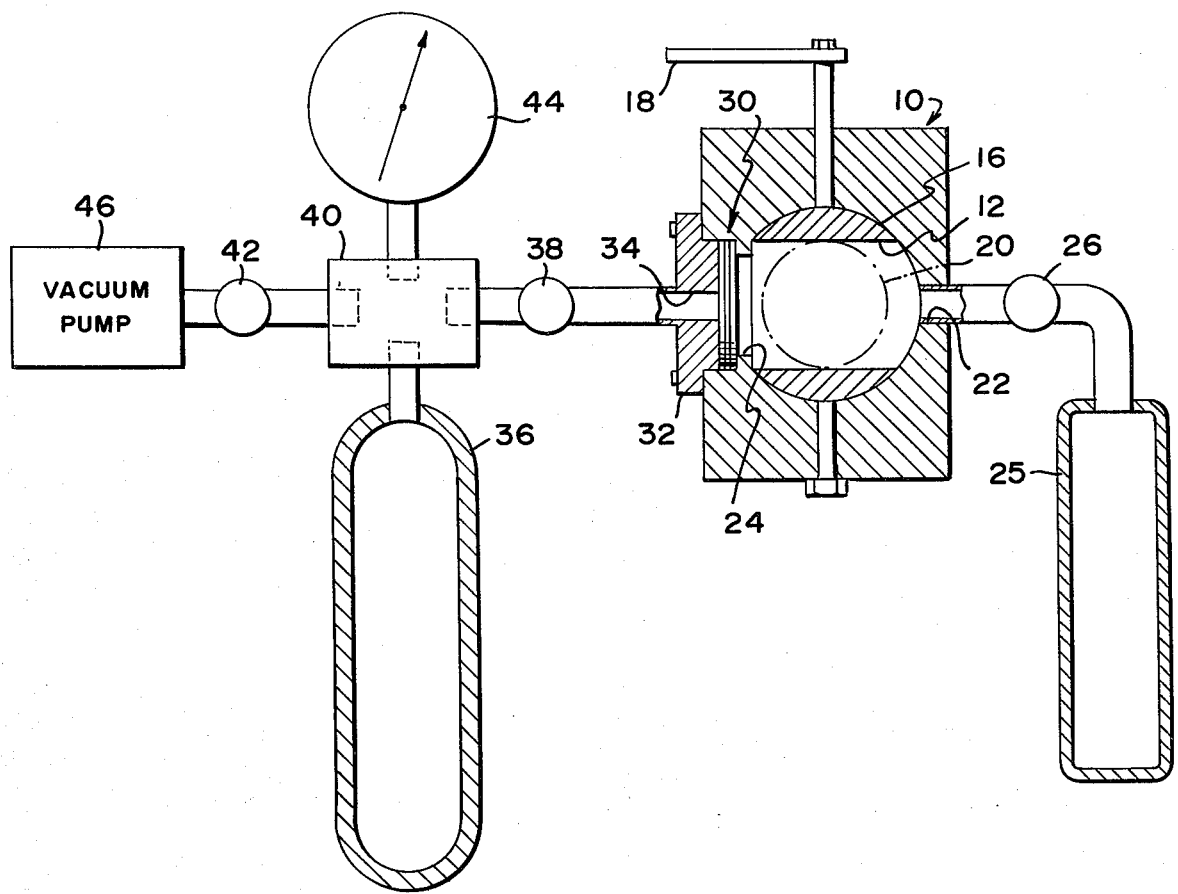
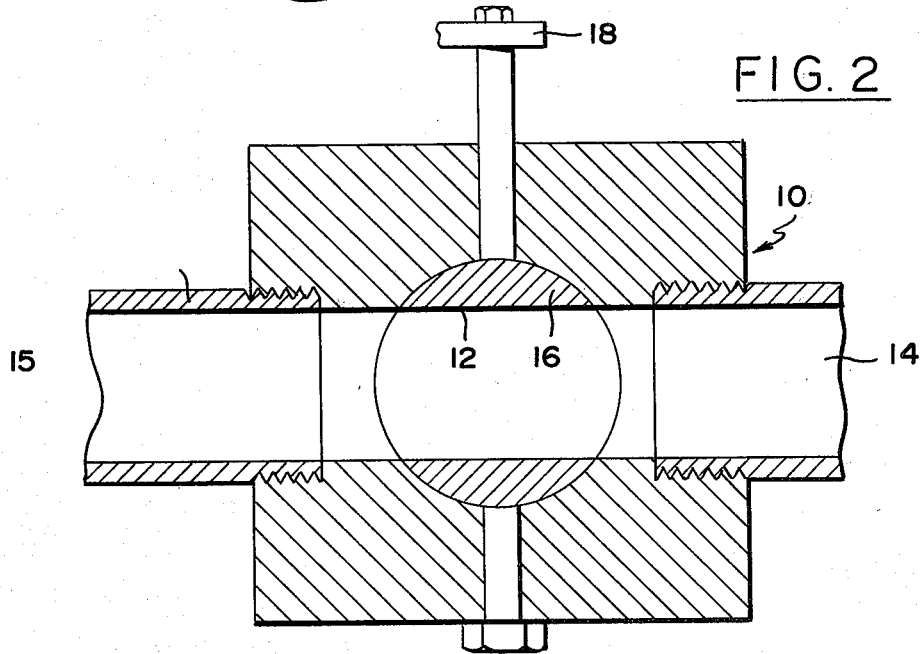

SAMPLER OF GAS BORNE PARTICLES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to an atmosphere sampler and, more particularly, to a sampler of gas-borne particles.

2. Description of the Prior Art

There are many applications in which it is desirable to sample small particles, contained in a gas, e.g., the atmosphere (air). This is generally performed by causing the air to pass through a filter which is designed to permit the air to pass therethrough while trapping the particles for subsequent analysis. One example of a prior art sampler of air-borne particles is described in U.S. Pat. No. 3,795,135. In said patent a filter arrangement is disclosed consisting of a plurality of filter discs with holes of different dimensions. These different filter discs are designed to trap particles of different dimensions. The need for a plurality of discs clearly increases the filter's complexity and cost.

OBJECTS AND SUMMARY OF THE INVENTION

It is a primary object of the present invention to provide a new sampler of gas-borne particles.

Another object of the present invention is to provide a relatively simple filter for trapping small particles borne by a gas.

Yet another object of the present invention is to provide a sampler of gas-borne particles in which particles with diameters less than the diameters of the holes in a single filter disc are trapped on the disc.

These and other objects of the invention are achieved by providing a sampler with a single filter disc or element with holes of small diameters. The gas, hereinafter generally assumed to be air, which contains the particles, is intimately mixed with a pressurized low molecular weight carrier gas and directed across the filter at a pressure differential, which is just below the rupture pressure of the filter element. The particles as used herein may be solid substances or liquid droplets. In such an arrangement particles with dimensions which are less than the diameters of the holes of the filter element become separated from the air. Thus, while the air passes through the holes of the filter element the smaller size particles impinge and become bound to the filter element. By admixing a carrier gas of low molecular weight, higher gas velocity is attainable for the same pressure differential. The particles rather than being clustered around the holes of the filter element are spread out over the element's surface between the holes, thereby enabling the analysis of the particles with less confusion than is now present when the particles are clustered together around the exit holes of the filter element.

The novel features of the invention are set forth with particularity in the appended claims. The invention will best be understood from the following description when read in conjunction with the accompanying drawings.

BRIEF DESCRIPTION OF THE DRAWINGS

FIG. 1 is a combination cross-section and block diagram of one embodiment of the invention;

FIG. 2 is a cross sectional view of a valve 10;

FIG. 3 is a view of the filter element in accordance with the present invention;

FIGS. *4a* and *4b* are useful in explaining the invention; and

FIG. 5 is a diagram of a filter assembly, actually reduced to practice.

DESCRIPTION OF THE PREFERRED EMBODIMENTS

Attention is now directed to FIG. 1 wherein numeral 10 designates a 90°ball cock valve, with a passageway 12 in which a sample of air, which contains particles to be analyzed is trapped. As shown in FIG. 2, which is a view of the valve 10 taken at 90°to its view in FIG. 1, an inlet tube 14, is threaded to the valve 10 at one end, while an outlet tube 15 is threaded to the valve at the other end. The passageway 12 is aligned with the inlet and outlet tubes. In use, air passes into the inlet tube 14, through the passageway 12 and out of the outlet tube 15 until it is desired to capture a sample in the passageway. This is done by rotating the ball 16 of valve 10, 90° by means of hand lever 18. The spherical sides of the ball 16 seal off both inlet and outlet tubes from the passageway, thus securing the sample in the passageway 12. In FIG. 1, the inlet and outlet tubes are indicated by the broken-line circle 20.

The passageway 12, in the position shown in FIG. 1, is provided with a samll threaded opening 22 in the valve body, as shown on the right, and a large counterbored recess 24 as shown on the left. A reservoir 25 is in communication with opening 22 through a control valve 26. The large recess 24 receives a filter assembly 30, which will be described hereinafter in detail. A flanged fitting 32 secures the filter assembly 30 in position, and through an opening 34 in fitting 32 connects the outlet end of the valve ball through the filter assembly 30 with a vacuum bottle 36, through a control valve 38. A four-way fitting 40 couples the vacuum bottle 36, the control valve 38, an exhaust valve 42 and a pressure indicator 44. The exhaust valve 42 is connected to a vacuum pump 46 to exhaust the vacuum bottle 36 prior to use and establish a low pressure, e.g., 50 Torr in the bottle 36.

The function of the reservoir 24 is to contain a carrier gas at high positive pressure, e.g., 100 or more atmospheres. In accordance with the present invention the carrier gas is one with a very low molecular weight, such as helium or hydrogen. As will be pointed out hereinafter for the same pressure differential conditions across assembly 30 higher flow velocities are attainable with a low molecular weight carrier gas than with a carrier gas of higher molecular weight, such as air.

In operation after the desired air sample is captured in passageway 12, as hereinbefore described, the control valves 26 and 38 are opened in sequence. The front face of the filter assembly 30, which is in communication with the passageway 12 and in essence forms one end thereof, is exposed to the high positive pressure of the carrier gas in reservoir 25. On the other hand, the back face or end of the filter assembly 30, which is in communication with the vacuum bottle 36, when valve 38 is open, is exposed to a negative (below atmosphere) pressure present in bottle 36. Thus, a substantial pressure difference is present across the filter assembly 30 when both valves 26 and 31 are opened.

The carrier gas in reservoir 25 which is at high pressure flows toward the low pressure point, i.e., toward bottle 36, and as it flows it forces the air sample with the particles entrained therein to flow ahead of it through the filter assembly 30. To simplify the following description no distinction will be made between the air and the carrier gas and the particles may be thought of as being entrained in the gas. All the gases and any particles, which pass through the filter assembly 30, are captured and retained in the vacuum bottle 36 for subsequent examination or are discharged through the exhaust valve 42.

In accordance with the present invention the pressure differential applied across the filter assembly 30 is just below the rupture point of the filter, in order to attain the highest possible flow velocity through the filter. Since the carrier gas is of low molecular weight the velocity with which the air sample as well as the carrier gas flow through the filter assembly is greater than the velocity which can be attained for the same pressure differential if a carrier gas of higher molecular weight is used. By maximizing the velocity with which the air sample is forced through the filter assembly very small particles, with diameters considerably smaller than the holes in the filter element, can be trapped with a single filter element.

In accordance with the present invention, the filter assembly 30 includes a single filter element or disc 50 (see FIG. 3) whose front surface 51 forms the front face of the filter assembly 30 and is in communication with the passageway 12. The filter element 50 has pore-like openings or holes 52. preferably the holes 52 are straight-through holes from surface 51 to the opposite filter element side 54. The holes define sharp corners at the exposed surface 51, as represented by the 90° corners shown in FIG. 3. The holes 52 may be of uniform diameters and uniformly distributed over surface 51, although such limitations are not always required. It is however very desirable that the filter element 50 be of minimal thickness in order to minimize the lengths of the holes 52 and thereby reduce the effect of the holes on the velocity of gases flowing through the holes of the filter element. In one embodiment, actually reduced to practice, the filter element 50 was of a thickness $t$ on the order of $10\mu$ with hole diameters on the order of $1\mu$, for a hole length to diameter ratio of 10:1.

Figure 4A:
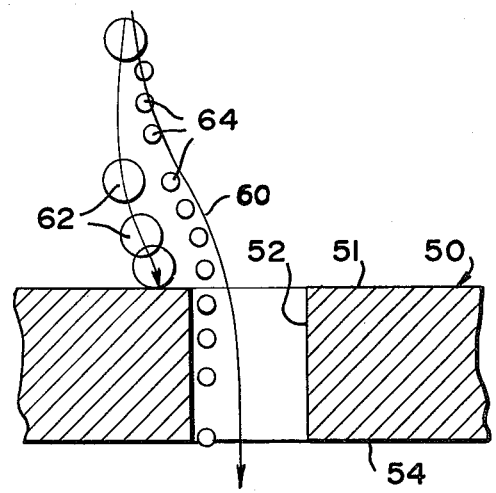

As shown in FIGS. 1 and 3 the filter element 50 of the filter assembly 30 is positioned in the path of the gas when valves 26 and 38 are opened. Due to the pressure differential the gas sample is forced through the holes 52 in the filter element 50. In each of FIGS. 4a and 4b only a single hole 52 of filter element 50 is shown. In FIG. 4a, numeral 60 designates the gas stream line as it approaches the filter element 50, and as it changes direction in order to pass through hole 52. Numerals 62 and 64 designate particles of different sizes entrained in the gas approaching the filter element 50. As the gas approaches the filter element 50, the gas flow direction or stream line changes so as to pass through the hole 52.

Figure 4B:
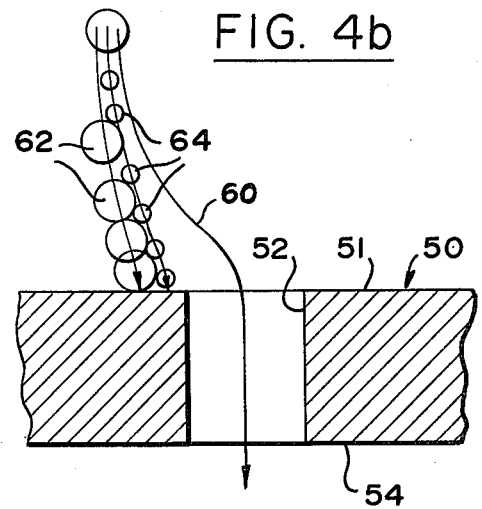

The ability of particles which are entrained in the gas to follow the change in the gas stream line, and therefore pass through the hole 52 with the gas, depends on the gas velocity. At the gas velocity, assumed for explanatory purposes for FIG. 4a, the small particles 64 which float in the gas are assumed to follow the gas as it changes direction to pass through the hole 52. Thus, these particles pass with the gas through the hole 52. However, at the particular gas velocity the larger diameter particles 62 do not follow the change in direction of the gas stream line. Therefore, as the gas stream line changes direction the larger particles 62 become separated from the gas. Instead of following the gas stream line through the hole they impact the surface 51 of the filter element 50 and become bound to the surface by van der Waals forces. In FIG. 4b, in which a higher gas velocity is assumed, even the smaller particles 64 cannot follow the change in the gas stream line and therefore they too become separated from the gas and are trapped on the surface 51 of the filter element 50, even though the diameters of particles 64 are less than the diameter of hole 52.

It should be stressed that in the present invention, the separation of the particles from the gas is not due to the fact that the particle diameters are greater than those of the hole 52, and therefore cannot pass therethrough. Rather, the separation is due to the fact that the gas velocity through the filter element 50 is made sufficiently high so that particles with diameters even less than the hole diameter, cannot follow the change in the direction of the gas stream line 60 and therefore, instead of remaining entrained in the gas, which passes through the hole, the particles become separated from the gas, as its stream line changes direction, and inpact the surface 51 of the filter element 50. Thus, it should be appreciated that for most efficient trapping of particles, the gas velocity should be as large as possible, taking into consideration the rupturing point of the filter element.

By using a low molecular weight carrier gas, such as He, in reservoir 25 as compared with air, a much higher velocity of gas is attained under the same pressure condition. Thus, the use of a low molecular weight carrier gas greatly contributes to particle trapping efficiency. As previously pointed out, the highest velocity is attainable by establishing a pressure differential which is just below the rupture pressure of the filter element 50 and using a low molecular weight carrier gas.

The filter element 50 should be as thin as practical so that the ratio of hole length to hole diameter is low, which results in highest gas velocity with lowest pressure differential. In a filter element with holes on the order of $1\mu$ in diameter the hole length, corresponding to the filter element thickness should preferably be on the order of $10\mu$.

Such a filter element is presently available at very reasonable cost in the form of a thin perforated sheet of polycarbonate plastic of about $10\mu$ in thickness, with straight-through holes on the order of $1\mu$ in diameter. The holes are formed by first exposing the sheet of plastic to collimated charged particles in a nuclear reactor. As the particles pass through the material they leave sensitized tracks which are then etched chemically with a hydroxide solution leaving uniform straight-through holes, on the order of $1\mu$ in diameter.

Such a filter element 50 has been used in one embodiment which was actually reduced to practice. However, since the filter element 50 was of plastic material it had to be protected from rupturing, due to the high pressure differentials. The protection was provided by including in the filter assembly 30 a perforated stainless steel backup plate 70, as shown in FIG. 5. The backup plate thickness was on the order of 1/16 inch, with openings 72 on the order of 100 microns in diameter on 250 micron centers. In order not to block the flow of gas through holes 52 of filter element 50, which were not aligned with openings 72 in the backup plate, a diffusion member 75 was included between the filter element 50 and the backup plate 70. The diffusion member 75 which was also on the order of 1/16 inch thick was a fibrous membrane, such as filter paper or glass wool paper to enable the gas passing through the holes 52 of filter element 50 to pass therethrough and therefrom through the openings 72 of the backup plate 70.

It is appreciated that the velocity of the gas through holes 52 which are not aligned with openings 72 is less than the gas velocity through aligned holes. However, with the diffusion member 75 at least some of the gas passes through holes 52 which are not aligned with openings 72. Thus, the overall trapping efficiency of particles by the filter element 50 is enhanced.

Figure 5:
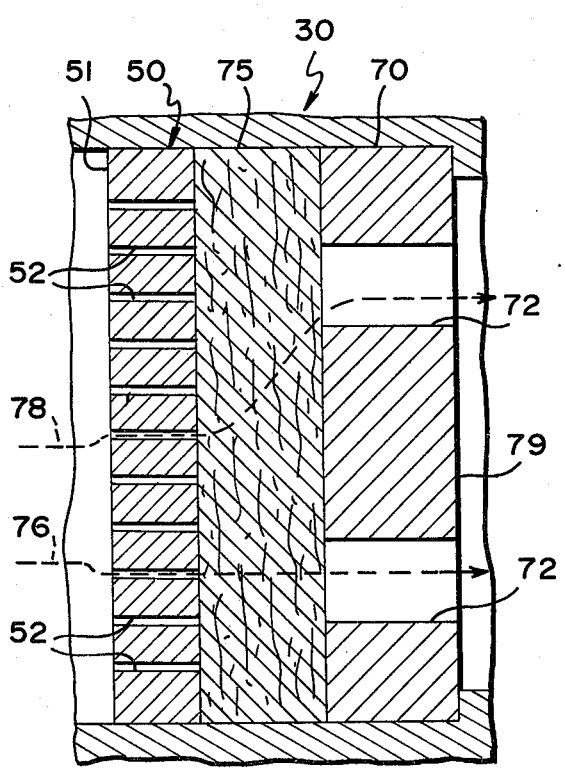

In FIG. 5 dashed line 76 represents the gas stream line through a hole 52 which is aligned with a hole 72 in backup plate 70, while dashed line 78 represents the gas stream line through a hole 52 which is not aligned with a hole 72, in the backup plate 70. in either case the gas passing through holes 52 in the single filter element 50 passes through the diffusion member 75 and therefrom through openings 72 of the backup plate 70. It should be clear that the dimensions of the various element and holes shown in FIG. 5 and the other figures are not to scale, but rather are presented to explain the features of the invention.

In the particular embodiment shown in FIG. 5 the front surface 51 of element 50 can be thought of as the first face or side of the filter assembly toward which the high velocity gas is directed while the back side 79 of backup 70 which is remote from the diffusion member 75 can be thought of as the back face or side of the filter assembly 30. The gas exits the assembly through the openings 72 into opening 34 (FIG. 1) and through valve 38 when open, and flows into the vacuum bottle 36, or through valve 42 if the gas sample is not to be saved.

It has been discovered that with the filter assembly of the present invention the particles such as 62 and 64 which become separated from the air in the atmosphere sample tend to spread out relatively uniformly on surface 51 of filter element 50 rather than be clustered around the edges of the holes 52. Consequently, the particles on the surface 51 can be examined later by for example a scanning electron microscope or by an electron probe X-ray microanalysis beam, with little confusion that is now present when all the particles tend to cluster together around the exit holes in conventional filter discs. It should be apparent that although hereinbefore the invention has been described in connection with an atmosphere sample, i.e., air containing particles, the invention can be used to separate particles entrained in any gas including those present in industrial processes.

Summarizing the foregoing description in accordance with the present invention, a single filter element with straightthrough holes is used to separate particles from a gas sample containing the particles, where the separated particle may be of smaller diameter than the diameters of the holes in the filter element. This is achieved by admixing the sample with a pressurized low molecular weight carrier gas and passing the gas mixture toward the filter element at a high optimum velocity due to the pressure differential created across the filter element. The pressure differential is preferably just below the rupture pressure of the filter element for the most effective results. As a result, particles with diameters, which are considerably smaller than the diameters of the holes in the filter element, become separated from the gas as the latter's stream line changes direction to pass through the holes. The separated particles become bound to the filter element surface and are relatively uniformly spread out over its surface for subsequent analysis.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A system for extracting at least some particles borne in a gas from said gas, comprising:
   valve means including a chamber for receiving a preselected amount of gas containing particles in said chamber;
   filter means disposed at one end of said chamber and including a single filter element with straight-through holes of preselected diameters; and
   drive means for establishing a pressure differential across said filter element which is just below the rupture pressure of said filter element and including a carrier gas of low molecular weight in communication with said chamber for forcing said gas containing said particles through the holes of said filter element at a velocity, whereby particles of dimensions less than the holes' diameters become separated from the gas, as the latter's stream line changes direction to pass through the holes, with the separated particles being bound to an exposed surface of the filter element.

2. The system as described in claim 1 wherein said pressure differential is on the order of 100 atmospheres and said filter element holes have diameters in the micron range.

3. The system as described in claim 2 wherein said filter element thickness is on the order of $10\mu$ and the hole diameters are on the order of $1\mu$.

4. The system as described in claim 3 wherein said carrier gas is selected from the group consisting of helium and hydrogen, and said particles include particles of diameters less than $1\mu$.

5. A system for extracting at least some particles borne in a gas sample from said gas sample, comprising:
   a single filter element with straight-through holes of diameters in the micron range extending between a top side of said filter element to an opposite side thereof;
   a source of low molecular weight carrier gas pressurized to a first pressure; and
   control means for forcing said gas sample by means of the pressurized carrier gas toward the top side of said filter element at a velocity whereby particles in said gas with diameters less than the holes' diameters become separated from the gas as the latter's stream line changes direction so as to pass through the holes in said filter element, with the separated particles becoming bound to the filter element on the top side thereof.

6. The system as described in claim 5 wherein said system includes a chamber containing said gas sample, with said filter element forming one side of said chamber, first communication means including a first control valve switchable to an open position to provide a path for said carrier gas into said chamber;

receiver means including a second control valve switchable to an open position in communication with the opposite side of said filter element, for establishing a second pressure less than said first pressure at said opposite side of said filter element, whereby when both said first and second control valves are in their open positions the pressure difference across said filter element is essentially equal to the difference between said first and second pressures, said pressure difference being just below the rupture pressure of said single filter element, and length to diameter ratio of said holes being on the order of 10:1.

7. The system as described in claim 6 wherein said first pressure is on the order of 100 atmospheres and said second pressure is below one atmosphere and said receiver means include a container for receiving the gas passing through the filter element holes and any particles passing therewith.

8. in a gas sampler of the type designed to separate at least some particles borne by the gas, the arrangement comprising;

a filter assembly including a filter element having a front surface and a back surface spaced apart a distance on the order of ten microns and having straight-through holes of diameters on the order of 1 micron between said surfaces, a backup plate with openings significantly greater than the diameters of the holes of said filter element, and a fibrous diffusion membrane located between said backup plate and said back surface of said filter element; and control means including a source of a carrier gas of low molecular weight and pressure control means for directing the gas bearing said particles toward said front face of said filter element with said carrier gas at a selected pressure differential, whereby as said gas stream line changes direction to pass through the holes in said filter element particles in the gas with diameters less than the hole diameters become separated from the gas and become bound to said filter element on the front face thereof, with the gas passing through the filter element holes flowing through said diffusion membrane and out of said filter assembly through the openings in said backup plate.

9. The sampler as described in claim 8 wherein said pressure differential is on the order of 100 atmospheres, said filter element is of a plastic material and said backup plate is of metal.

10. The sampler as described in claim 8 wherein the carrier gas is selected from the group consisting of helium and hydrogen.

\* \* \* \* \*